(12) United States Patent
Ichizawa et al.

(10) Patent No.: US 8,829,459 B2
(45) Date of Patent: Sep. 9, 2014

(54) RADIATION DETECTION APPARATUS

(75) Inventors: Yasushi Ichizawa, Musashino (JP); Hirohiko Obinata, Musashino (JP); Yuusaku Koga, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 932 days.

(21) Appl. No.: 12/973,213

(22) Filed: Dec. 20, 2010

(65) Prior Publication Data

US 2011/0147603 A1    Jun. 23, 2011

(30) Foreign Application Priority Data

Dec. 22, 2009    (JP) .................... 2009-290614

(51) Int. Cl.
*G01T 1/185* (2006.01)
*G01N 33/34* (2006.01)
*G01N 23/16* (2006.01)

(52) U.S. Cl.
CPC .............. *G01T 1/185* (2013.01); *G01N 33/346* (2013.01); *G01N 23/16* (2013.01)
USPC ........................................................ 250/375

(58) Field of Classification Search
USPC .................... 250/375, 389, 385.1, 390.03
See application file for complete search history.

(56) References Cited

U.S. PATENT DOCUMENTS 4,727,561 A * 2/1988 Fujisaki ........................... 378/54
5,959,302 A * 9/1999 Charpak ................... 250/385.1

FOREIGN PATENT DOCUMENTS

| CN | 1126316 A | 7/1996 | |
|---|---|---|---|
| JP | 03059487 A * | 3/1991 | ............... G01T 1/16 |
| JP | 2728986 B2 | 12/1992 | |
| JP | 04359856 A | 12/1992 | |
| JP | 2002040142 A | 2/2002 | |
| JP | 2003-329430 A | 11/2003 | |
| JP | 2006522331 A | 9/2006 | |
| WO | WO 2004080130 A2 | 9/2004 | |

OTHER PUBLICATIONS

Japanese Office Action corresponding to Japanese Patent Application No. Q2009-290614, mailed Sep. 1, 2011.

* cited by examiner

*Primary Examiner* — David Porta
*Assistant Examiner* — Faye Boosalis
(74) *Attorney, Agent, or Firm* — Sughrue Mion, PLLC (57) ABSTRACT

A radiation detection apparatus includes a radiation detection unit that detects a first intensity of a radiation that has been transmitted through an inspection target to generate a first measurement value, the inspection target being disposed between a radiation source that irradiates the radiation and the radiation detection unit, a transmission ionization chamber that detects a second intensity of the radiation that has not reached the inspection target to generate a second measurement value, the transmission ionization chamber having an enclosed structure, the transmission ionization chamber being disposed between the radiation source and the inspection target, the transmission ionization chamber including an entrance window through which the radiation enters the transmission ionization chamber and an exit window through which the radiation goes out of the transmission ionization chamber, and an operation unit that calculates a physical quantity of the inspection target.

9 Claims, 7 Drawing Sheets

RADIATION DETECTION APPARATUS

BACKGROUND OF THE INVENTION

1. Field of the Invention

The present invention relates to a radiation detection apparatus that detects radiation, such as X-rays or β-rays. More specifically, the present invention relates to a radiation detection apparatus that reduces the attenuation of radiation in a gas until radiation irradiated from a radiation source reaches an object to be measured and stabilizes the output of radiation.

Priority is claimed on Japanese Patent Application No. 2009-290614, filed Dec. 22, 2009, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

In recent years, inspection using X-rays has spread in terms of quality control in food, industrial products, and the like or security management. In many cases, it is not a soft X-ray, which is much absorbed by air, but a hard X-ray, which is less absorbed by air, that is used. However, there are also samples for which transmission characteristics can be obtained only through the use of the soft X-ray due to the properties thereof.

A soft X-ray including an extremely short ultraviolet ray can be employed in various research fields and inspection fields of food, industry, medical services, security, and the like. Further, the latent demand for the soft X-ray is very large. Since a soft X-ray is absorbed well by air or a solvent, the transmitting performance of a soft X-ray is low. Accordingly, it is difficult to measure a soft X-ray in the air or a solution. There have been many cases where it is difficult to inspect a sample having an appropriate thickness by a transmission method using a soft X-ray.

Figure 6A:
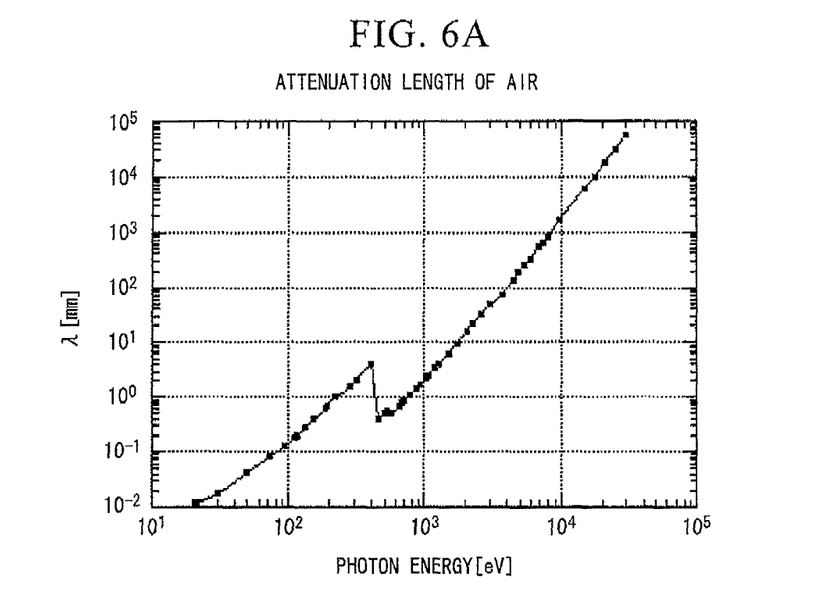
FIG. 6A is a view illustrating a relationship between the energy of X-rays and an attenuation length where X-rays are absorbed by air and the energy of the X-rays is thus attenuated to 1/e.

FIG. 6A is a view showing a relationship, which is disclosed at http://pfwww.kek.jp/kitajima/sx/sxme.html, between the energy of X-rays and an attenuation length λ where X-rays are absorbed by air and the energy of the X-rays is thus attenuated to 1/e. The horizontal axis represents the energy of X-rays. The vertical axis represents an attenuation length λ where X-rays having an energy of 0.02 to 30 keV are transmitted through air having a pressure of 1 atmosphere and the energy of the X-rays is attenuated to 1/e. When the energy of the X-rays is 10 keV, an attenuation length λ is about 2 m. An attenuation length λ is 0.1 m when the energy of the X-rays is 4 keV, and an attenuation length λ is 0.01 m when the energy of the X-rays is 2 keV.

Likewise, X-rays are much absorbed by a window material used in the window that partitions the atmospheric pressure and the vacuum in a radiation detection apparatus. A material, which absorbs a small amount of X-rays, has been used as the window material to a limited extent.

Figure 6B:
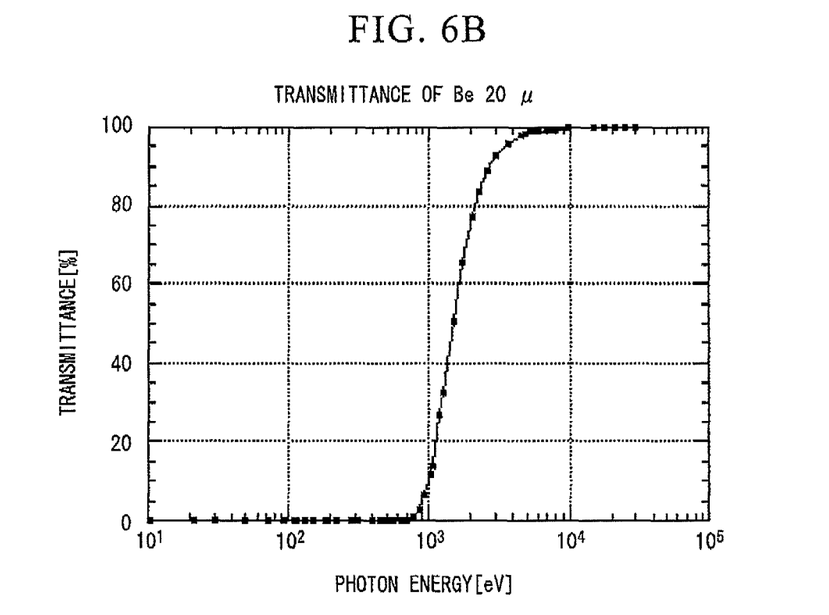
FIG. 6B is a view illustrating a relationship between the energy of X-rays and the transmittance of beryllium having a thickness of 20 μm.

FIG. 6B is a view disclosed at the above-mentioned URL, and is a view showing a relationship between the energy of X-rays and the transmittance of beryllium having a thickness of 20 μm that is a typical window material. When the energy of X-rays is 5 keV or more, the transmittance of beryllium is 95% or more. When the energy of the X-rays is 1 keV or less, the transmittance of beryllium is 10% or less. Diamond or $Si_3N_4$ having a thickness of about 0.4 μm may be used as the window material.

Figure 7A:
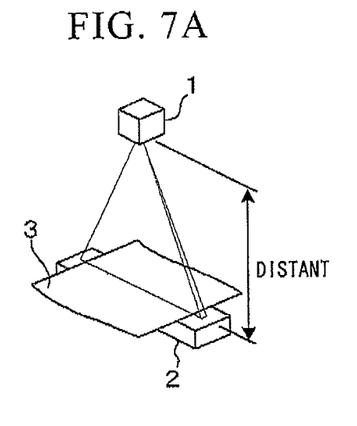
FIG. 7A is a schematic perspective view illustrating an example of a radiation detection apparatus in accordance with the related art.

FIG. 7A is a view showing an inspection device in the related art that uses X-rays or β-rays. A sheet-like object or sample to be inspected 3 is disposed between the beam source 1 of X-rays or β-rays and a radiation detector 2 such as a line sensor, a digital camera with a scintillator, and an ionization box. The sample 3 is installed so as to be distant from one beam source 1 by a certain distance. Radiation is radially diffused from the beam source 1 in the width direction of the sample 3, and is irradiated to the sample 3. The mixing of foreign materials, the presence or absence of components, the presence or absence of defects, and the uniformity of materials of film thickness, an ingredient, and the like are determined from the transmission characteristics of the sample 3.

If the device is further provided with a direct conversion type radiation detection element detector such as a CdTe capable of discriminating energy, it may also be possible to discriminate energy.

Transmission measurement and inspection in a relatively narrow range is used in research or the fields of food and medical services. Meanwhile, in many cases, transmission measurement in a wide range is used in the fields of industrial products or security.

If a sample 3 is provided so as to be distant from one beam source 1 that radially diffuses radiation in the width direction of the sample 3 as shown in FIG. 7A and radiation is irradiated in a wide range and detected by a radiation detector 2 such as a camera or a line sensor for covering a wide range, inspection in a wide range can be also performed by one beam source and one detector. In this case, even if air does not absorb radiation, the radiation dose is reduced substantially in proportion to the square of the distance. Accordingly, a beam source 1 having a high output is required.

The radiation tube current is increased, so that a large dose of radiation may be irradiated. Since a soft X-ray is absorbed by air, beam hardening occurs. The beam hardening is a phenomenon where when continuous radiation is transmitted through a material, low energy radiation is absorbed more than high energy radiation, so that an energy peak of the radiation is shifted to a high energy peak. It is not possible to inspect the sample at a distance due to the occurrence of beam hardening. When beam hardening occurs, the dose of absorbed radiation is not sufficient in the case of a sample having high transparency. Accordingly, detection sensitivity is not obtained. Further, a detection signal level is lowered, so that detection accuracy deteriorates. Further, in the soft X-ray inspection in the related art, a set of a beam source 1, a radiation detector 2, a sample 3, a conveying device, and the like is sealed in vacuum in a shield chamber. In the case of air, a sample 3 is installed close to the beam source 1 and a narrow range is observed.

Figure 7B:
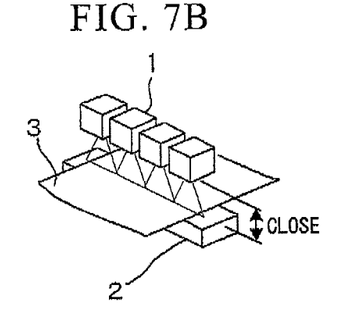
FIG. 7B is a schematic perspective view illustrating an example of a radiation detection apparatus in accordance with the related art.

FIG. 7B is a view showing another example of an inspection device in the related art that uses X-rays or β-rays. In FIG. 7B, a plurality of beam sources 1 is arranged in line so that the distance between the beam source 1 and the sample 3 is smaller than in the inspection device shown in FIG. 7A. Accordingly, a wide range is collectively detected.

If there is variation of the dose of radiation irradiated from the beam source 1, the measurement of the dose of transmitted radiation is directly affected. For this reason, measurement accuracy deteriorates. When it is to be determined whether an illegal device or an object, a metal piece, and the like exist in security management or food control, variation of several-percent in the dose of radiation irradiated from the beam source 1 is not a problem.

The stability of the dose of radiation irradiated from the beam source 1 is very important in the measurement of the thickness of a paper or resin sheet, a thin metal film, and the like. It may be possible to exclude the influence of the variation of the dose of radiation, which is irradiated from the beam source 1, by measuring the dose of radiation, which is not yet transmitted through the sample 3, and subtracting the dose of radiation, which is not yet transmitted through the sample 3, from the dose of radiation that has been transmitted through the sample 3. Accordingly, the transmittance of the sample 3 is accurately obtained.

In general, it may be possible to obtain transmission characteristics of the radiation in regard to a sample 3 using one detector, by measuring the dose of transmitted radiation in a state where a sample 3 exists and in a state where a sample 3 does not exist and taking a difference therebetween.

Figure 7C:
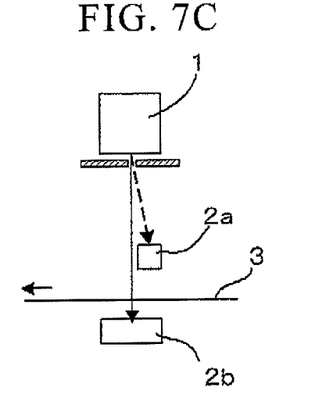
FIG. 7C is a side view illustrating an example of a radiation detection apparatus in accordance with the related art.

FIG. 7C is a view showing a measuring device of an in-line apparatus in the related art when the sample 3 is a product, such as a paper or resin sheet, continuously produced without being cut. Two radiation detectors 2a and 2b are installed so that a sample 3 is interposed therebetween. The detector 2a measures the dose of radiation that is not transmitted through a sample 3 yet. The detector 2a is disposed above the sample 3 on the side of the beam source 1. The detector 2b measures the dose of radiation transmitted through the sample 3. The detector 2b is disposed below the sample 3. Since the plurality of detectors 2a and 2b is provided as described above, it may be possible to measure and correct the variation of the dose of radiation in real time.

Another radiation detection apparatus is provided with one radiation detector that has a size larger than the width of the sample 3. In this case, the device measures online the dose of radiation, which is not yet transmitted through a sample 3, by emitting radiation to the range wider than the width of the sample 3 and measuring the dose of radiation at a portion where radiation directly reaches the radiation detector 2.

The beam source 1 has a limited lifetime, and needs to be replaced about once every several years. The beam source 1 is expensive. Since the beam source 1 is installed in a temperature control device, it is difficult to replace the beam source. For this reason, the beam source 1 requires large running costs. If a plurality of beam sources 1 is provided, running costs corresponding to the number of the beam sources are required. For this reason, the number of beam sources 1 needs to be reduced as much as possible.

Meanwhile, if a set of the beam source 1, the radiation detector 2, the sample 3, the conveying device, and the like is sealed in vacuum in the shield chamber as described above, the device needs to be strongly made as a whole. Accordingly, the price of the device becomes high as a whole. The input and output of the sample 3 are troublesome and time is required to form a vacuum. For this reason, the device is very poor in terms of use. Further, if the sample 3 is a continuous body such as a sheet, it is not easy to form a vacuum state.

In order to emit radiation in the wide range, the sample 3 needs to be distant from the beam source 1. Accordingly, since the amount of radiation absorbed by air is further increased and beam hardening occurs, it may not be possible to use radiation in the low-energy range that is advantageous for the measurement of transmission characteristics.

A gap between the beam source 1 and the sample 3 is generally open to the air. For this reason, the amount of radiation absorbed by air is changed due to the influence of the temperature of air, atmospheric pressure, humidity, and the like. This change becomes a factor of a measurement error.

Highly accurate measurement is particularly required for the measurement of the thickness of a thin film. Since a slight variation of the dose of radiation directly affects measurement accuracy, the control of the stability of the radiation irradiated from the beam source 1 is essential.

In general, it may be possible to cope with the change of the sensitivity of the detector and the short-term and long-term change of the dose of radiation by correcting the sensitivity of the detector or the variation of the dose of radiation, when the sample 3 is removed, every several hours to several days. The frequency of correction is high, the correction is troublesome, and the change of the dose of radiation cannot be fed back in real time. An expensive high-performance power supply for the beam source 1 is employed, and it necessary to manage the temperature of a measuring instrument or a beam source 1 and the temperature and humidity of an ambient environment.

If a plurality of radiation detectors is used as shown in FIG. 7C, larger costs, installation space, and the like are required.

Japanese Unexamined Patent Application, First Publication No. 2003-329430 discloses a line sensor or a radiation detector that can detect the variation of radiation irradiated from one or two beam sources 1 but cannot detect the radiation irradiated from three or more beam sources 1. Further, the line sensor measures the end portions of radiation flux. For example, the end portions of radiation flux are different from the middle portion of the radiation flux. Furthermore, the measured result is different from the variation of the total amount of the radiation flux.

SUMMARY

A radiation detection apparatus may include a radiation source that irradiates a radiation, a radiation detection unit that detects a first intensity of the radiation that has been transmitted through an inspection target to generate a first measurement value, the inspection target being disposed between the radiation source and the radiation detection unit, a transmission ionization chamber that detects a second intensity of the radiation that has not yet reached the inspection target to generate a second measurement value, the transmission ionization chamber having an enclosed structure, the transmission ionization chamber being disposed between the radiation source and the inspection target, the transmission ionization chamber including an entrance window through which the radiation enters the transmission ionization chamber and an exit window through which the radiation goes out of the transmission ionization chamber, and an operation unit that calculates a physical quantity of the inspection target based on the first measurement value and the second measurement value.

The transmission ionization chamber may detect the second intensity of the radiation and generates the second measurement value in real time. The transmission ionization chamber may feed back the second measurement value to the radiation source so as to control the radiation source.

The transmission ionization chamber may be formed in a trapezoidal shape so that the length of a portion of the transmission ionization chamber corresponding to the exit window is larger than that of a portion of the transmission ionization chamber corresponding to the entrance window.

The transmission ionization chamber may be filled with a gas that absorbs a small amount of radiation.

The gas may include at least one of He (helium gas), $H_2$ (hydrogen gas), $CH_4$ (methane gas), $H_2O$ (water vapor), Ne (neon gas), $O_2$ (oxygen gas), and $N_2$ (nitrogen gas).

The gas may be filled at atmospheric pressure or a pressure slightly lower than the atmospheric pressure.

The transmission ionization chamber may include a first parallel plate electrode and a second parallel plate electrode. The first parallel plate electrode and the second parallel plate electrode may be disposed in parallel to each other so as to face each other with a predetermined distance therebetween. The radiation irradiated from the radiation source may pass between the first and second parallel plate electrodes while the first parallel plate electrode serves as a negative electrode and the second parallel plate electrode serves as a positive electrode.

The entrance window and the exit window may be formed of at least one of a thin Be (beryllium) film, polyethylene, a PET (polyethylene terephthalate) film, an aluminum deposited PET film, and a composite PET member laminated by a thin aluminum film.

The radiation detection apparatus may further include an electrometer that is connected to the first parallel plate electrode, the electrometer detecting the second intensity of the radiation by measuring an electric current from the first parallel plate electrode, the electrometer generating the second measurement value.

A radiation detection apparatus may include a radiation detection unit that detects a first intensity of a radiation that has been transmitted through an inspection target to generate a first measurement value, the inspection target being disposed between a radiation source that irradiates the radiation and the radiation detection unit, a transmission ionization chamber that detects a second intensity of the radiation that has not reached the inspection target to generate a second measurement value, the transmission ionization chamber having an enclosed structure, the transmission ionization chamber being disposed between the radiation source and the inspection target, the transmission ionization chamber including an entrance window through which the radiation enters the transmission ionization chamber x and an exit window through which the radiation goes out of the transmission ionization chamber, and an operation unit that calculates a physical quantity of the inspection target based on the first measurement value and the second measurement value.

The transmission ionization chamber may detect the second intensity of the radiation and generates the second measurement value in real time. The transmission ionization chamber may feed back the second measurement value to the radiation source so as to control the radiation source.

The transmission ionization chamber may be formed in a trapezoidal shape so that the length of a portion of the transmission ionization chamber corresponding to the exit window is larger than that of a portion of the transmission ionization chamber corresponding to the entrance window.

The transmission ionization chamber may be filled with a gas that absorbs a small amount of radiation.

The gas may include at least one of He (helium gas), $H_2$ (hydrogen gas), $CH_4$ methane gas), $H_2O$ (water vapor), Ne (neon gas), $O_2$ (oxygen gas), and $N_2$ (nitrogen gas).

The gas may be filled at atmospheric pressure or a pressure slightly lower than the atmospheric pressure.

The transmission ionization chamber may include a first parallel plate electrode and a second parallel plate electrode. The first parallel plate electrode and the second parallel plate electrode may be disposed in parallel to each other so as to face each other with a predetermined distance therebetween. The radiation irradiated from the radiation source may pass between the first and second parallel plate electrodes while the first parallel plate electrode serves as a negative electrode and the second parallel plate electrode serves as a positive electrode.

The entrance window and the exit window may be formed of at least one of a thin Be (beryllium) film, polyethylene, a PET (polyethylene terephthalate) film, an aluminum deposited PET film, and a composite PET member laminated by a thin aluminum film.

The radiation detection apparatus may further include an electrometer that is connected to the first parallel plate electrode, the electrometer detecting the second intensity of the radiation by measuring an electric current from the first parallel plate electrode, the electrometer generating the second measurement value.

A radiation detection method may include performing a first detection of a first intensity of a radiation that has passed through an inspection target to generate a first measurement value, the inspection target being disposed between a radiation source that irradiates the radiation and a radiation detection unit that performs the first detection, performing a second detection of a second intensity of the radiation that has not reached the inspection target to generate a second measurement value, the second detection being performed in a transmission ionization chamber having an enclosed structure, the transmission ionization chamber disposed between the radiation source and the inspection target, and calculating a physical quantity of the inspection target based on the first measurement value and the second measurement value.

The radiation detection method may further include feeding back the second measurement value to the radiation source so as to control the radiation source. The second detection of the second intensity of the radiation and the generating of the second measurement value may be done in real time.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

A radiation detection apparatus in accordance with the preferred embodiments of present invention does not generate beam hardening even though using radiation such as soft X-rays or β-rays, which are much absorbed by air. Further, the radiation detection apparatus in accordance with the preferred embodiments of present invention can detect radiation in a wide range even though the number of beam sources is small. The radiation detection apparatus in accordance with the preferred embodiments of present invention can measure the dose of radiation, which is irradiated from the beam source, in real time and stabilize the dose of radiation that is irradiated from the beam source. Since the radiation detection apparatus in accordance with the preferred embodiments of present invention can correct a measurement error caused by the variation of the dose of radiation, it may be possible to achieve highly accurate measurement. The radiation detection apparatus in accordance with the preferred embodiments of present invention can reduce the cost of the device, improve measurement sensitivity, reduce the output of the beam source, and lengthen the lifetime of the beam source.

The radiation detection apparatus in accordance with the preferred embodiments of present invention includes a transmission ionization chamber having an airtight structure between the radiation source and the sample. The transmission ionization chamber includes a radiation entrance window and a radiation exit window. The radiation detection apparatus detects the dose of radiation that is not yet transmitted through a sample. The radiation detection apparatus compares and calculates the measured values of the dose of radiation, which is not yet transmitted through a sample and has been transmitted through the sample, in real time, and can correct the variation of the dose of radiation irradiated from the beam source.

The radiation detection apparatus in accordance with the preferred embodiments of present invention may perform a control for feeding back the intensity of radiation, which is measured in real time by the transmission ionization chamber, to the radiation source. Accordingly, the radiation detection apparatus can stably control the intensity of radiation that is irradiated from the beam source, Further, it may be possible to correct the deterioration of output that is caused by the variation of a power supply, the change in temperature, and the variation with time of the beam source.

The absorption of radiation in the air also significantly depends on floating matter in the form of dust and dirt in the air. Since the radiation detection apparatus in accordance with the preferred embodiments of present invention has an airtight structure, it may be possible to completely exclude floating matter and a stable detection result may be expected.

In the radiation detection apparatus in accordance with the preferred embodiments of present invention, the transmission ionization chamber may be formed in a trapezoidal shape so that the length of a portion of the transmission ionization chamber corresponding to the radiation exit window is larger than that of a portion of the transmission ionization chamber corresponding to the radiation entrance window. The container having an airtight structure may be filled with a gas that absorbs less radiation in a single gas or gas mixture thereof. The gas may be formed of He (helium gas), $H_2$ (hydrogen gas), $CH_4$ (methane gas), $H_2O$ (water vapor), Ne (neon gas), $O_2$ (oxygen gas), $N_2$ (nitrogen gas), and the like. As a result, in the radiation detection apparatus in accordance with the preferred embodiments of present invention, beam hardening is controlled, so that it may be possible to perform measurement, such as the measurement of the thickness of a thin film, using the energy range of radiation where the absorption characteristics of radiation in a low-energy range are large and measurement with high sensitivity can be performed. Therefore, measurement sensitivity is improved.

Further, in the radiation detection apparatus in accordance with the preferred embodiments of present invention, the output of the beam source can be reduced, so that the cost of a radiation tube can be reduced or the lifetime of the radiation tube can be lengthened.

Furthermore, it may be possible to significantly reduce the influence of change of humidity, temperature, or atmospheric pressure caused by the weather, and a stable detection result may be expected.

In the radiation detection apparatus in accordance with the preferred embodiments of present invention, the transmission ionization chamber may be filled with the gas at atmospheric pressure or a pressure slightly lower than atmospheric pressure. The chamber does not need to have a strong structure, and it may be possible to form a highly reliable ionization box at low costs.

In the radiation detection apparatus in accordance with the preferred embodiments of present invention, first and second parallel plate electrodes may be installed in the transmission ionization chamber. The first parallel plate electrode serves as a negative electrode, and the second parallel plate electrode serves as a positive electrode. The first and second parallel plate electrodes are installed so as to face each other with a predetermined distance therebetween, and radiation passes between the electrodes. It may be possible to detect the radiation, which passes between the first and second parallel plate electrodes, with a simple structure.

In the radiation detection apparatus in accordance with the preferred embodiments of present invention, the material of the entrance window and the exit window of the transmission ionization chamber may be a material that includes a thin Be (beryllium) film, polyethylene, a PET (polyethylene terephthalate) film, an aluminum deposited PET film, and a composite PET member laminated by a thin aluminum film. Accordingly, it may be possible to reduce the attenuation of radiation at the windows of the transmission ionization chamber.

The present invention will be now described herein with reference to illustrative embodiments. Those skilled in the art will recognize that many alternative embodiments can be accomplished using the teaching of the present invention and that the present invention is not limited to the embodiments illustrated herein for explanatory purposes.

Figure 1:
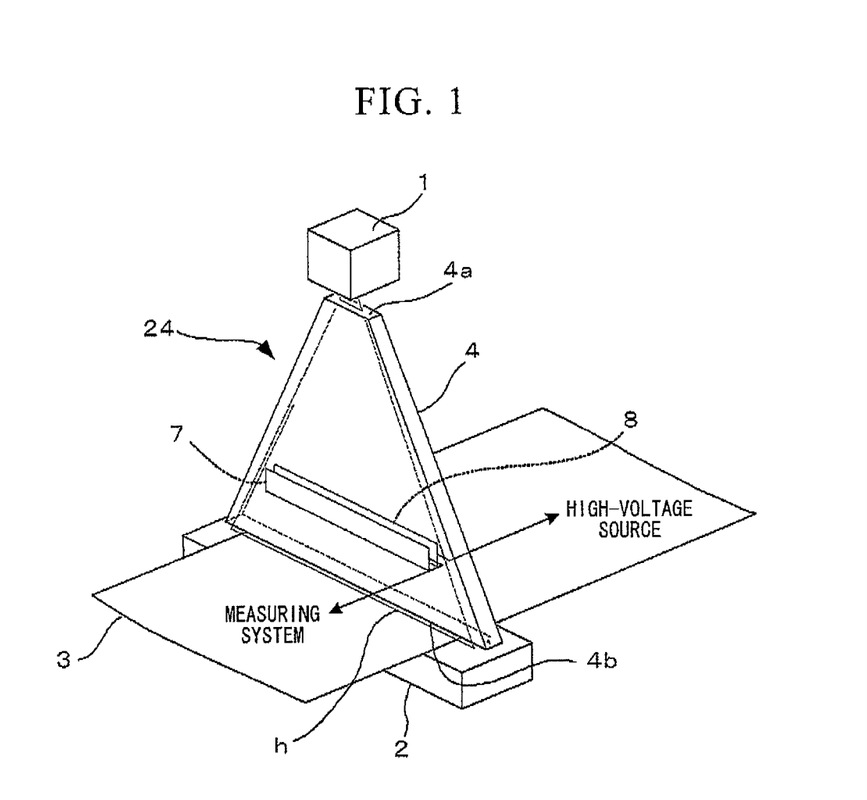
FIG. 1 is a schematic perspective view illustrating an example of a radiation detection apparatus in accordance with a first preferred embodiment of the present invention.

A first preferred embodiment of the present invention will be described. FIG. 1 is a schematic perspective view illustrating an example of a radiation detection apparatus in accordance with a first preferred embodiment of the present invention. As in FIG. 7A, a beam source 1 for X-rays, β-rays, or the like is installed so as to face a line sensor 2, that is, a radiation detector. A sample 3, which is an object to be inspected, is disposed at a position distant from the beam source 1, and comes into contact with an upper portion of the line sensor 2 or is disposed slightly above the line sensor 2. The sample 3 is moved in a direction substantially perpendicular to the direction where radiation is irradiated. In the example of FIG. 1, the sample 3 is moved in the horizontal direction. Radiation h is irradiated from the beam source 1 toward the line sensor 2 and the sample 3. The radiation h is transmitted through the sample 3, and the dose of the radiation transmitted through the sample 3 is detected by the line sensor 2. Accordingly, the measurement and detection of the sample 3 are performed. Meanwhile, the radiation dose is the intensity of radiation.

FIG. 1 is different from FIG. 7A in that a transmission ionization chamber 24 is interposed between the beam source 1 and the sample 3. The transmission ionization chamber 24 includes a shield chamber 4 that is a shield member for preventing the leakage of radiation. The shield chamber 4 may be made of Fe, stainless used steel, or the like.

A collimator or an irradiation tube, which is not illustrated in the figures, may be disposed at a position directly behind a position where radiation is irradiated from the beam source 1. Accordingly, extra radiation, which does not contribute to measurement, is limited and irradiated to the line sensor 2 and the sample 3. If a distance between the beam source 1 and the sample 3 or a distance between the beam source 1 and the line sensor 2 is large, the shield chamber 4 for surrounding the entire side surface of the path of radiation is installed so that a gap through which radiation leaks is not formed. Accordingly, the leakage of radiation is prevented.

Even though a lead plate or the like is not used in shielding, it may be possible to sufficiently block a soft X-ray by a simple structure that is surrounded by an aluminum material or an iron plate having a thickness of several millimeters. Since the radiation corresponding to a low-energy range such as a soft X-ray is significantly affected by scattering, the surrounding region of the path of radiation needs to be covered. In particular, if the beam source 1 is at a great distance, the shield chamber 4 is essential to prevent the leakage of radiation and secure safety.

In the first preferred embodiment of present invention, thin films 4a and 4b are formed on the upper and lower surfaces of the shield chamber 4. The thin films are made of beryllium, polypropylene, or the like that is a material that absorbs a small amount of radiation.

Appropriate ionization characteristics are achieved by the reduction of the pressure in the transmission ionization chamber 24. For this purpose, the thin film 4a formed on the upper surface of the transmission ionization chamber 24 and the thin film 4b formed on the lower surface of the transmission ionization chamber should be formed to have a thickness corresponding to the strength at which depressurization can be withstood.

When the thin films 4a and 4b are formed with a large thickness so as have the strength at which reduced pressure can be withstood, radiation is absorbed by the thin films 4a and 4b even if the thin films 4a and 4b are made of beryllium or the like that is a material that absorbs a small amount of radiation. Therefore, measurement sensitivity deteriorates.

Parallel plate electrodes 7 and 8 are installed on the inner surface of the transmission ionization chamber 24 so as to face each other with high insulation. The parallel plate electrodes 7 are connected to a measuring system. The parallel plate electrodes 8 are connected to a high-voltage source. Radiation or radiation flux passes between the parallel plate electrodes 7 and 8. The parallel plate electrodes 7 and 8 are disposed at an appropriate distance so that the passage of radiation is not hindered.

The parallel plate electrodes 7 and 8 include at least one set of electrodes. If the diffusion angle of radiation is large or an irradiation distance is large, that is, if the entire radiation dose cannot be measured by one set of electrodes provided near the middle of the parallel plate electrodes 7 and 8, a plurality of electrodes may be provided at the middle, both ends, or the like of the parallel plate electrodes 7 and 8.

Figure 2:
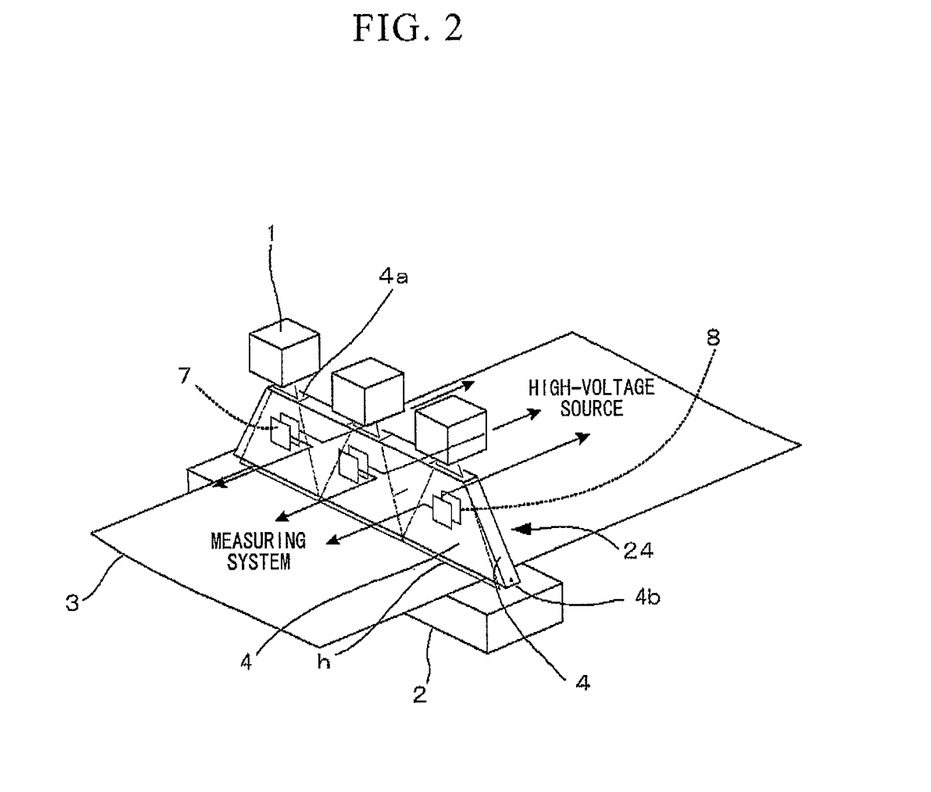
FIG. 2 is a schematic perspective view illustrating another example of the radiation detection apparatus in accordance with a first preferred embodiment of the present invention.

FIG. 2 is a schematic perspective view illustrating another example of the radiation detection apparatus in accordance with a first preferred embodiment of the present invention. In FIG. 2, a plurality of beam sources 1 is provided and parallel plate electrodes 7 and 8 are provided for each of the beam sources 1. Three beam sources 1 are provided in the example of FIG. 2. A transmission ionization chamber 24 is filled with gas which is lighter than air and of which pressure is reduced to about atmospheric pressure or pressure withstood by window materials. He (helium) is preferable as the gas lighter than air. However, single gases or gas mixtures, which contain a gas capable of reducing the radiation absorption of a gas, such as $H_2$ (hydrogen gas), $CH_4$ (methane gas), $H_2O$ (water vapor), Ne (neon gas), $O_2$ (oxygen gas), and $N_2$ (nitrogen gas), as a major ingredient, may be used as other gases lighter than air.

Figure 3:
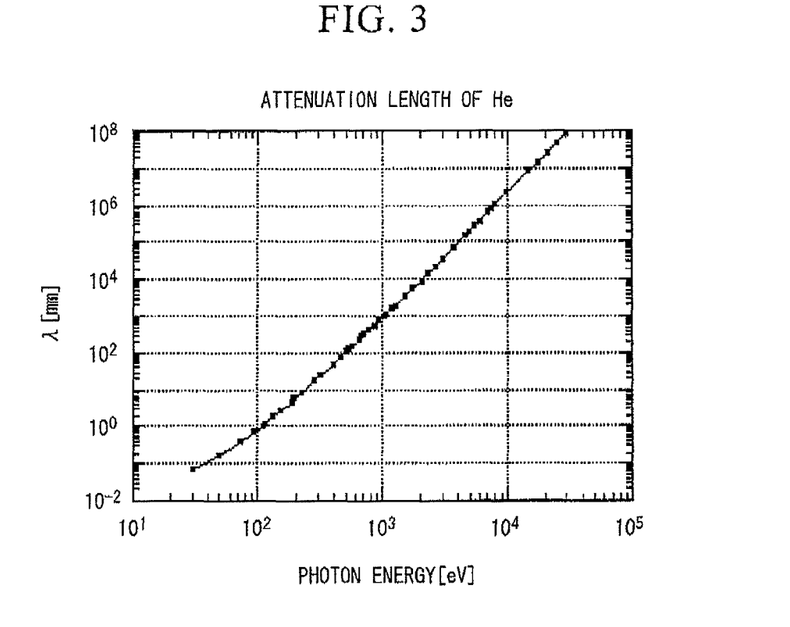
FIG. 3 is a view illustrating a relationship between the energy of X-rays and an attenuation length where X-rays are absorbed by helium and the energy of the X-rays is thus attenuated to 1/e.

FIG. 3 is a view illustrating a relationship between the energy of X-rays and an attenuation length where X-rays are absorbed by helium and the energy of the X-rays is thus attenuated to 1/e. An attenuation length $\lambda$ is 20,000 m when the energy of X-rays is 20 keV, an attenuation length $\lambda$ is 1,000 m when the energy of X-rays is 1 keV, and an attenuation length $\lambda$ is 0.1 m when the energy of X-rays is 500 eV, FIG. 3 shows that X-rays can be transmitted through helium by about $\lambda$ mm, Meanwhile, X-rays are attenuated by air several hundreds to several thousands times more as compared to helium.

In FIG. 1, a collimator, which is not illustrated in the figures, is provided at an emission end of each of the beam sources 1 from which radiation is irradiated. The collimator limits a region to which radiation not contributing to radiation detection is irradiated. For example, if the diffusion angle of radiation is 30°, that is, if radiation is diffused at an angle of about 60° in the whole angle, it is preferable that the distance between the beam source 1 and the sample 3 be about twice the length of a range where radiation is irradiated. Accordingly, from FIG. 3, if the length of the range where radiation is irradiated, that is, a detection region is about several millimeters or less, it may be possible to sufficiently suppress the absorption of radiation in the air.

While a large amount of radiation is transmitted through the gas filled in the transmission ionization chamber 24, ionization occurs by a part of the radiation. For this reason, a gas, which is formed by mixing a little gas having a high degree of ionization to a gas having low atomic weight, may be used as the filled gas.

Figure 4:
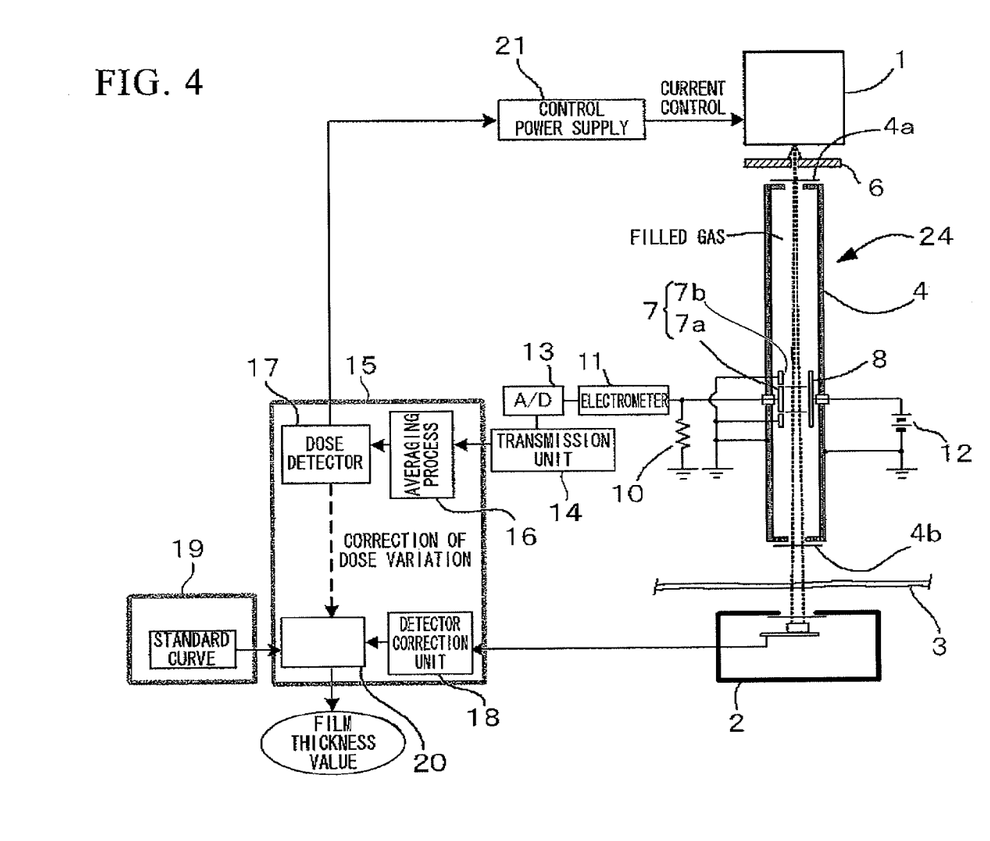
FIG. 4 is a partial cross-sectional view and a partial block diagram illustrating the radiation detection apparatus of FIG. 1.

FIG. 4 is a partial cross-sectional view and a partial block diagram illustrating the radiation detection apparatus of FIG. 1. Radiation is irradiated from the beam source 1 to the line sensor 2 and the sample 3. A collimator 6 is provided at an emission end of the beam source 1 from which radiation is irradiated. In FIG. 4, the collimator 6 collimates the radiation, which is irradiated from the beam source 1, in parallel. The radiation, which has passed through the collimator 6, passes through the transmission ionization chamber 24 that is formed of the shield chamber 4. The parallel plate electrodes 7 and 8 are installed in the transmission ionization chamber 24 so as to face each other. The parallel plate electrode 7 includes a collector electrode 7a and a guard electrode 7b. The collector electrode 7a is grounded through a high resistor 10 that has high accuracy. Accordingly, the collector electrode 7a is insulated from the shield chamber 4, the guard electrode 7b, and the parallel plate electrode 8. The entire periphery of the collector electrode 7a is surrounded by the guard electrode 7b. The guard electrode 7b and the shield chamber 4 are grounded with a low impedance. The collector electrode 7a is connected to an electrometer 11 that measures very small current. The other parallel plate electrode 8, which is disposed so as to face the parallel plate electrode 7, is a high-voltage electrode. The parallel plate electrode 8 is installed so as to be highly insulated from the parallel plate electrode 7, and is connected to a high-voltage source 12.

The collector electrode 7a is connected to the high resistor 10. The electrometer 11 measures a voltage value corresponding to the radiation dose, that is, the intensity of radiation. The voltage value measured by the electrometer 11 is converted into a digital signal by the A/D-conversion of an A/D converter 13, and is transmitted to an operation unit 15 through a transmission unit 14.

The operation unit 15 includes an averaging processor 16, a dose detector 17, a detector correction unit 18, and a transmitted dose operating unit 20. The averaging processor 16 performs an averaging process of a signal transmitted from the transmission unit 14.

The dose detector 17 measures the dose of radiation that is not yet transmitted through the sample 3.

A signal, which corresponds to the dose of radiation detected by the dose detector 17, is sent to a control power supply 21. The control power supply 21 outputs control current for controlling the intensity of radiation irradiated from the beam source so that the intensity of the radiation becomes constant.

Further, a signal, which corresponds to the dose of the radiation detected by the dose detector 17, is monitored by the transmitted dose operating unit 20.

The radiation transmitted through the sample 3 is measured by the line sensor 2. The output signal of the line sensor 2 is corrected by the detector correction unit 18, and is sent to the transmitted dose operating unit 20. The transmitted dose operating unit 20 calculates a film thickness value from the output signal of the line sensor 2 that is corrected by the detector correction unit 18 and a standard curve that is stored in a storage unit 19. The storage unit 19 stores a standard curve that is correction data.

The line sensor 2 is a scintillator-type detector.

According to the above-mentioned structure, the dose of the radiation, which is not transmitted through the sample 3 yet and is detected in the transmission ionization chamber 24, is transmitted to the operation unit 15 that operates the measured result of the line sensor 2. This dose of the radiation is compared with the dose of the radiation, which has been transmitted through the sample 3 and is detected by the line sensor 2, in real time. As a result, it may be possible to accurately correct the film thickness value in regard to the variation of the dose of the radiation irradiated from the beam source 1. In the past, it was not possible to monitor the variation of the dose of the radiation irradiated from the beam source 1 during the measurement of the sample 3. In the radiation detection apparatus in accordance with the preferred embodiments of present invention, it is possible to monitor the variation of the dose of the radiation irradiated from the beam source 1. Further, if the dose of the radiation, which is not yet transmitted through the sample 3, is calculated and retained in the long term, it may be possible to reduce the regular management, such as the maintenance of the dose of radiation irradiated from the beam source 1 when the dose of the radiation irradiated from the beam source 1 is equal to or smaller than a predetermined dose, the replacement of the beam source 1, and the adjustment of the gain of the measuring system.

The variation of the dose of the radiation, which is irradiated from the beam source 1 and is not yet transmitted through the sample 3, is detected in the transmission ionization chamber 24, and is fed back to the control power supply 21 that controls the beam source 1, so that it may be possible to stably control the beam source 1. Accordingly, it may be possible to correct the variation of a power supply, the change in temperature, the deterioration of the output of the beam source 1 that is caused by the variation with time of the beam source 1, and the like. A method of controlling the beam source 1 controls the current of the beam source 1 by PID control, PI control, or the like, which is generally used, so as to make the output value of the transmission ionization chamber 24 become a constant value.

Figure 5:
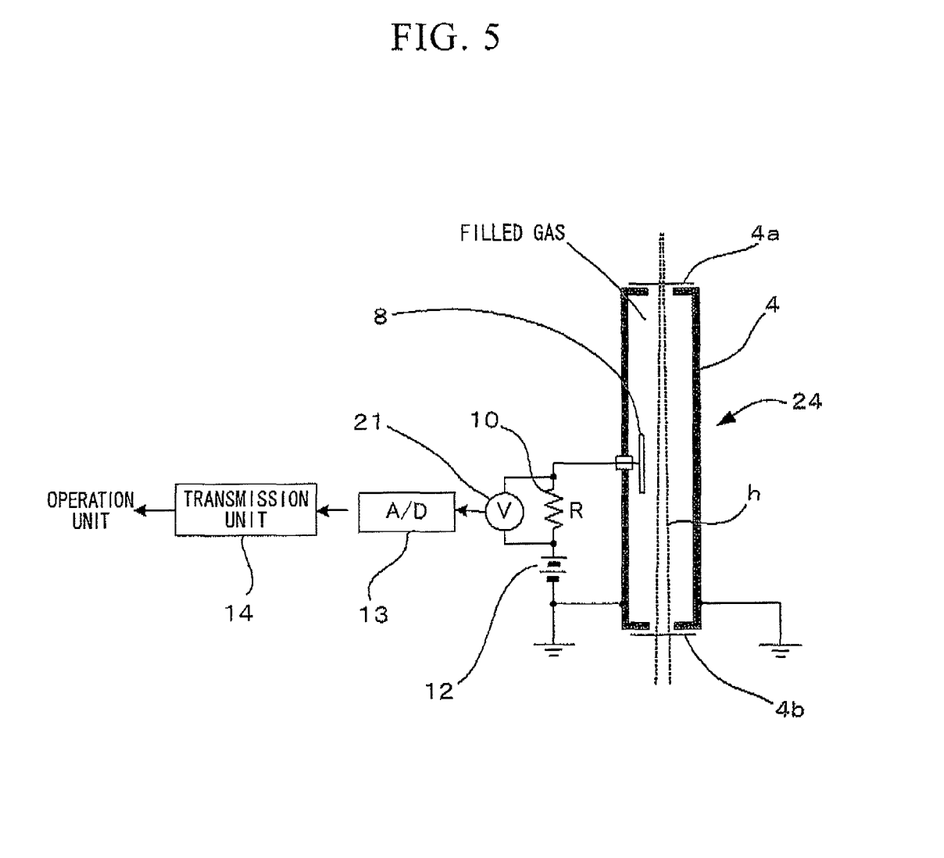
FIG. 5 is a partial cross-sectional view and a partial block diagram illustrating another example of the radiation detection apparatus of FIG. 1.

FIG. 5 is a partial cross-sectional view and a partial block diagram illustrating another example of the radiation detection apparatus of FIG. 1. A parallel plate electrode 8 is installed on one side of a shield chamber 4. The parallel plate electrode 8 has a unit structure that includes a pair of electrodes, and detects the radiation h near the path of radiation. According to this structure, the mounting position of the electrode can be easily changed and assemblability is improved. In FIG. 5, the same components as those of FIG. 4 are denoted by the same reference numerals.

In this embodiment, the parallel plate electrode 8 is held so as to be highly insulated from the transmission ionization chamber 24. The parallel plate electrode 8 is connected to a high resistor 10, and the high resistor 10 is connected to a high voltage 12. That is, the parallel plate electrode 8 is connected to the high voltage 12 through the high resistor 10. The high voltage 12 is applied to the parallel plate electrode 8 through the high resistor 10, so that the parallel plate electrode 8 becomes a survey meter attracting ionized electrons. This is a method that is generally used to detect very small current.

A voltmeter 21 is connected to both ends of the high resistor 10. The voltmeter 21 is connected to the A/D converter 13. A current signal from the parallel plate electrode 8 is converted into a voltage signal by the voltmeter 21. The voltage signal is converted into a digital signal by the A/D converter 13, and is sent to the operation unit through the transmission unit 14. Since the signal processing after the operation unit is the same as that shown in FIG. 4, the description thereof will be omitted here.

Meanwhile, as the parallel plate electrode 8, a pair of electrodes may be provided in one shield chamber 4 and a plurality of small electrodes may be installed. The electrode is not limited. Further, the size of the parallel plate electrode 8, that is, the width, the height, and the shape of the parallel plate electrode 8 are not limited.

As described above, in accordance with the preferred embodiments of present invention, the parallel plate electrode is installed in the transmission ionization chamber 24, a high voltage is applied to the parallel plate electrode 8, and the dose of radiation passing through the transmission ionization chamber 24 is measured. The difference between the above-mentioned transmission ionization chamber 24 and the ionization box in the related art will be described below.

(1) A transmission ionization chamber 24 in accordance with the preferred embodiments of present invention includes not only a radiation entrance window but also a radiation exit window.

(2) The transmission ionization chamber 24 in accordance with the preferred embodiments of present invention does not have the size of the transmission ionization chamber 24 that is fitted to the parallel plate electrode, and has a relatively large size according to the range where radiation is irradiated.

(3) In the ionization box in the related art, a distance between the parallel plate electrodes is made to be sufficiently larger than the range of incident radiation, photons, or charged particles. After the incident radiation, photons, or charged particles are completely stopped and all the energy is lost, all of the positive ions and electronic ions generated according to the range are collected. In the radiation detection apparatus in accordance with the preferred embodiments of present invention, the radiation, which is not yet transmitted through the sample 3, is measured.

(a) In the preferred embodiments of present invention, single gases or gas mixtures, which contain a gas lighter than air barely attenuating radiation by the radiation absorption of the gas, such as He (helium), $H_2$ (hydrogen gas), $CH_4$ (methane gas), $H_2O$ (water vapor), Ne (neon gas), $O_2$ (oxygen gas), and $N_2$ (nitrogen gas), as a major ingredient, are used as the gas filled in the transmission ionization chamber 24. Gases, such as Ar (argon gas), Xe (xenon gas), and Kr (krypton gas), are easily ionized when charged particles pass through the gases. Each of the above-mentioned gases is heavier than air and the density thereof is larger than that of the air.

(b) In (a), the transmission ionization chamber 24 has been filled with the gas lighter than air. However, since it is particularly difficult to ionize He (helium) and $H_2$ (hydrogen gas), a small amount of gases, which are easily ionized, may be mixed to He (helium) and $H_2$ (hydrogen gas) as long as the attenuation of radiation caused by absorption does not deteriorate. Further, $CH_4$ (methane gas), $H_2O$ (water vapor), Ar (argon gas), Xe (xenon gas), or Kr (krypton gas) may be mixed to He (helium). A mixing ratio thereof is adjusted according to the output of the transmission ionization chamber 24.

(4) The transmission ionization chamber 24 in accordance with the preferred embodiments of present invention is formed of a shield chamber 4 that has a volume larger than the volume of a common ionization box. In order to increase the transmission distance of radiation, the transmission ionization chamber is adapted to reduce the attenuation of radiation caused by absorption of gas and to make radiation be generally transmitted through the gas.

(5) Since the radiation dose used in the transmission ionization chamber 24 in accordance with the preferred embodiments of present invention is larger than that used in the ionization box in the related art, the size of the electrode, the distance between the electrodes, and a voltage applied to the electrode are optimized by the control of the voltage of the beam source 1 and the output of the beam source 1.

(6) Since the shield chamber 4 is large in terms of the transmission ionization chamber 24 in accordance with the preferred embodiments of present invention, it may be possible to select the position where the electrode is optimum. Since the dose of the transmitted radiation per unit area is proportional to the inverse square of the distance from the beam source 1 at the upper and lower portions of the shield chamber 4, a distance where the distance between the beam source 1 and the electrode becomes optimum is selected according to the output of the electrode.

Meanwhile, the above description is to merely describe a specific preferred embodiment for the purpose of the exemplification and description of the present invention. For example, radiation has been detected by the parallel plate electrode in the embodiment, but a coaxial cylinder type electrode may be used. No matter how airtight a container is, the pressure in the container is also changed if the container is used for several years. In this case, if a constant pressure generating source including a diaphragm and a coil spring is mounted in the container at a part of the container, it may be possible to keep constant pressure without being affected by the variation of the external atmospheric pressure even though the filled gas leaks.

The shape of the shield chamber 4 is not limited to the shape disclosed in the embodiment. The shield chamber has a pyramid shape in regard to an area sensor and has a circular arc shape in regard to a sensor arranged along the surface. That is, the shape of the shield chamber may be changed to an appropriate shape according to the use condition thereof.

Further, an auxiliary tank, which is provided with a decompression valve and is filled with the same gas as the filled gas, is mounted on the transmission ionization chamber in order to cope with the leakage of the filled gas. Accordingly, it may be possible to stabilize pressure.

Furthermore, the shield chamber 4 does not need to be formed separately from the beam source 1 and may have a continuous structure, or may have an integrated structure where the beam source 1 is disposed in the shield chamber 4, If the shield chamber has this structure, the entrance window of the shield chamber 4 may be removed. Accordingly, it may be possible to reduce the attenuation of the dose of radiation.

In the preferred embodiments of present invention, the radiation source 1 may not be included in the radiation detection apparatus. The radiation source 1 and the radiation detection apparatus may be separated.

As used herein, the following directional terms "forward, rearward, above, downward, vertical, horizontal, below, and transverse" as well as any other similar directional terms refer to those directions of an apparatus equipped with the present invention. Accordingly, these terms, as utilized to describe the present invention should be interpreted relative to an apparatus equipped with the present invention.

The term "configured" is used to describe a component, section or part of a device includes hardware and/or software that is constructed and/or programmed to carry out the desired function.

Moreover, terms that are expressed as "means-plus function" in the claims should include any structure that can be utilized to carry out the function of that part of the present invention.

The terms of degree such as "substantially," "about," "nearly", and "approximately" as used herein mean a reasonable amount of deviation of the modified term such that the end result is not significantly changed. For example, these terms can be construed as including a deviation of at least ±5 percents of the modified term if this deviation would not negate the meaning of the word it modifies.

The term "unit" is used to describe a component, section or part of a hardware and/or software that is constructed and/or programmed to carry out the desired function. Typical examples of the hardware may include, but are not limited to, a device and a circuit.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. A radiation detection apparatus comprising:
a radiation detection unit that detects a first intensity of a radiation that has been transmitted through an inspection target to generate a first measurement value, the inspection target being disposed between a radiation source that irradiates the radiation and the radiation detection unit;
a transmission ionization chamber that detects a second intensity of the radiation that has not reached the inspection target to generate a second measurement value, the transmission ionization chamber having an enclosed structure, the transmission ionization chamber being disposed between the radiation source and the inspection target, the transmission ionization chamber including an entrance window through which the radiation enters the transmission ionization chamber and an exit window through which the radiation goes out of the transmission ionization chamber; and an operation unit that calculates a physical quantity of the inspection target based on the first measurement value and the second measurement value, wherein the transmission ionization chamber detects the second intensity of the radiation and generates the second measurement value in real time, and the transmission ionization chamber feeds back the second measurement value to the radiation source so as to control the radiation source.

2. The radiation detection apparatus according to claim 1, wherein the transmission ionization chamber is filled with a gas that absorbs a small amount of radiation.

3. The radiation detection apparatus according to claim 2, wherein the gas includes at least one of He (helium gas), $H_2$ (hydrogen gas), $CH_4$ (methane gas), $H_2O$ (water vapor), Ne (neon gas), $O_2$ (oxygen gas), and $N_2$ (nitrogen gas).

4. The radiation detection apparatus according to claim 2, wherein the gas is filled at atmospheric pressure or a pressure slightly lower than the atmospheric pressure.

5. The radiation detection apparatus according to claim 1, wherein the transmission ionization chamber includes a first parallel plate electrode and a second parallel plate electrode, the first parallel plate electrode and the second parallel plate electrode are disposed in parallel to each other so as to face each other with a predetermined distance therebetween, and the radiation irradiated from the radiation source passes between the first and second parallel plate electrodes while the first parallel plate electrode serves as a negative electrode and the second parallel plate electrode serves as a positive electrode.

6. The radiation detection apparatus according to claim 1, wherein the entrance window and the exit window are formed of at least one of a thin Be (beryllium) film, polyethylene, a PET (polyethylene terephthalate) film, an aluminum deposited PET film, and a composite PET member laminated by a thin aluminum film.

7. The radiation detection apparatus according to claim 5, further comprising: an electrometer that is connected to the first parallel plate electrode, the electrometer detecting the second intensity of the radiation by measuring an electric current from the first parallel plate electrode, the electrometer generating the second measurement value.

8. A radiation detection apparatus comprising:
a radiation detection unit that detects a first intensity of a radiation that has been transmitted through an inspection target to generate a first measurement value, the inspection target being disposed between a radiation source that irradiates the radiation and the radiation detection unit;

a transmission ionization chamber that detects a second intensity of the radiation that has not reached the inspection target to generate a second measurement value, the transmission ionization chamber having an enclosed structure, the transmission ionization chamber being disposed between the radiation source and the inspection target, the transmission ionization chamber including an entrance window through which the radiation enters the transmission ionization chamber and an exit window through which the radiation goes out of the transmission ionization chamber; and an operation unit that calculates a physical quantity of the inspection target based on the first measurement value and the second measurement value, wherein the transmission ionization chamber is formed in a trapezoidal shape so that the length of a portion of the transmission ionization chamber corresponding to the exit window is larger than that of a portion of the transmission ionization chamber corresponding to the entrance window.

9. A radiation detection method comprising:

performing a first detection of a first intensity of a radiation that has passed through an inspection target to generate a first measurement value, the inspection target being disposed between a radiation source that irradiates the radiation and a radiation detection unit that performs the first detection;

performing a second detection of a second intensity of the radiation that has not reached the inspection target to generate a second measurement value, the second detection being performed in a transmission ionization chamber having an enclosed structure, the transmission ionization chamber disposed between the radiation source and the inspection target; and calculating a physical quantity of the inspection target based on the first measurement value and the second measurement value, wherein performing the second detection of the second intensity of the radiation and generating the second measurement value in real time, and feeding back the second measurement value to the radiation source so as to control the radiation source.

* * * * *